United States Patent [19]

Combs

[11] Patent Number: 5,081,242

[45] Date of Patent: Jan. 14, 1992

[54] 6-BENZOXAZINYL- AND 6-BENZOTHIAZINYL 2,3,4,5-TETRAHYDROPYRIDAZIN-3-ONES

[75] Inventor: Donald W. Combs, Piscataway, N.J.

[73] Assignee: Ortho Pharmaceutical Corporation, Raritan, N.J.

[21] Appl. No.: 657,254

[22] Filed: Feb. 15, 1991

Related U.S. Application Data

[63] Continuation of Ser. No. 125,142, Dec. 2, 1987, abandoned, and a continuation-in-part of Ser. No. 64,638, Jun. 22, 1987, Pat. No. 4,766,118, and a continuation-in-part of Ser. No. 944,316, Dec. 22, 1986, Pat. No. 4,721,784.

[51] Int. Cl.$^5$ .................. C07D 765/36; C07D 279/16
[52] U.S. Cl. .......................... 544/52; 544/51; 544/105
[58] Field of Search ............................ 544/51, 52, 105

[56] References Cited

U.S. PATENT DOCUMENTS

| | | | |
|---|---|---|---|
| 3,770,734 | 11/1973 | Pesson et al. | 544/105 |
| 4,400,318 | 8/1983 | Weaver et al. | 544/105 X |
| 4,619,687 | 10/1986 | Haga et al. | 544/105 X |
| 4,640,707 | 2/1987 | Nagano et al. | 544/105 X |
| 4,778,792 | 10/1988 | Lesieiur et al. | 514/230.5 |
| 4,816,454 | 3/1989 | Zollen et al. | 514/211 |

FOREIGN PATENT DOCUMENTS

| | | |
|---|---|---|
| 223674 | 5/1987 | European Pat. Off. . |
| 853519 | 3/1986 | Finland . |
| 1560628 | 3/1969 | France . |
| 2013678 | 8/1979 | United Kingdom . |

OTHER PUBLICATIONS

Combs et al., J. Med. Chem., vol. 33 (1990), pp. 380-386.

*Primary Examiner*—Richard L. Raymond
*Attorney, Agent, or Firm*—Benjamin F. Lambert

[57] ABSTRACT

The synthesis of benzoxazinyl- and benzothiazinyl-pyridazinone compounds is described. The novel compounds are cardiotonic agents and inhibitors of phosphodiesterase. In addition, the compounds are useful as smooth muscle relaxants and bronchodilators.

8 Claims, No Drawings

6-BENZOXAZINYL- AND 6-BENZOTHIAZINYL 2,3,4,5-TETRAHYDROPYRIDAZIN-3-ONES

This is a continuation of application Ser. No. 07/125,142 filed Dec. 2, 1987 which is a continuation-in-part of application Ser. No. 64,638, filed June 22, 1987, now U.S. Pat. No. 7,766,118, which in turn is a continuation-in-part of application Ser. No. 944,316, filed Dec. 22, 1986, now U.S. Pat. No. 4,721,484.

BACKGROUND OF THE INVENTION

1. Field of the Invention

The present invention relates to compounds of the formula:

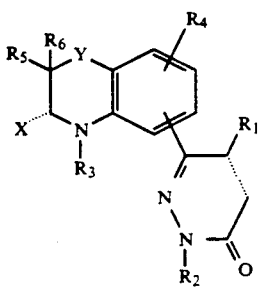

I as further defined herein. The compounds are useful as cardiotonic and vasodilating agents and as inhibitors of phosphodiesterase fraction III and platelet aggregation. In addition, the compounds are active as smooth muscle relaxants and bronchodilators. The present invention further relates to intermediates of these compounds as further defined herein.

2. Description of the Prior Art

Quinoline substituted pyridazin-3-ones have been shown to be cardiotonic agents and platelet aggregation inhibitors. Published European Patent Application No. 155,798 and British Patent No. 2,031,404 describe compounds of the formula:

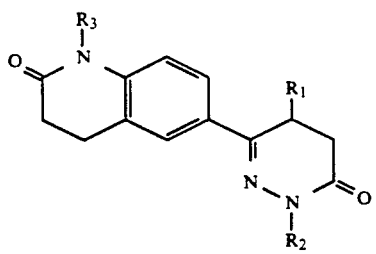

where $R_1$, $R_2$ and $R_3$ may be H or lower alkyl.

U.S. Pat. No. 4,562,190 describes benzothiazole substituted pyridazin-3-ones of the formula

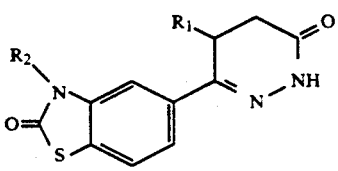

III where $R_1$ is $C_1$–$C_6$ alkyl and $R_2$ is H, $C_1$–$C_6$ alkyl or aryl.

SUMMARY OF THE INVENTION

The present invention is directed to 6-benzoxazinyl- and 6-benzothiazinyl-2,3,4,5-tetrahydropyridazin-3-ones of the general formula:

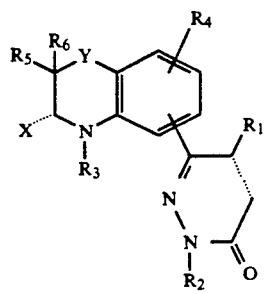

I where
 X may be $H_2$ or O;
 Y may be O or S;
 $R_1$ may be H, $C_{1-6}$ straight- or branched-chain alkyl or $C_{3-6}$ cycloalkyl;
 $R_2$ may be H, $C_{1-6}$ straight- or branched-chain alkyl, $C_{3-6}$ cycloalkyl or $C_{2-6}$ alkenyl;
 $R_3$ may be H, $C_{1-6}$ straight- or branched-chain alkyl or $C_{3-6}$ cycloalkyl, and when X is $H_2$, $R_3$ may also be $C_2$–$C_6$ acyl, arylacyl such as benzoyl and phenylacetyl, or alkanesulfonyl such as methanesulfonyl;
 $R_4$ may be H, halogen, $C_{1-6}$ straight- or branched-chain alkyl or $C_{1-6}$ alkoxy;
 $R_5$ and $R_6$ may each be H, $C_{1-6}$ straight- or branched-chain alkyl or $C_{3-6}$ cycloalkyl; and
 the dotted line may be a single or double bond between C4 and C5 of the pyridazine ring.

The compounds of formula I are useful as cardiotonic agents having a long duration of activity and are very potent inhibitors of phosphodiesterase fraction III.

The present invention is further directed to intermediates of the compounds of formula I having the general formulas of

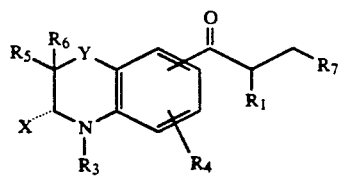

IV

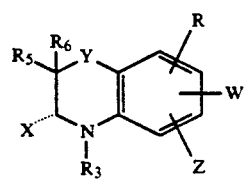

V where
 $R_1$, $R_3$, $R_4$, $R_5$ and $R_6$ may independently be H, $C_{1-6}$ straight- or branched-chain alkyl or $C_{3-6}$ cycloalkyl;
 $R_7$ may be H, $C_{1-6}$ straight- or branched-chain alkyl, -CN or mono- or di-$C_{1-6}$ alkyl amino;
 X may be $H_2$ or O;
 Y may be O or S;

R, W and Z may independently be H, $C_{1-6}$ straight- or branched-chain alkyl, $C_{2-6}$ acyl or —C(O)CHR$_4$CH$_2$C(O)OR$_8$; and R$_8$ may be H or $C_{1-6}$ straight- or branched-chain alkyl.

In the intermediates of the general formula IV, when R$_7$ is —CN or mono- or di-$C_{1-6}$ alkyl amino, the intermediates may also include the quaternary ammonium salts thereof.

In the intermediates of the general formula V, R$_3$ may also be $C_{2-6}$ acyl, arylacyl or $C_{1-6}$ alkylsulfonyl when X is H$_2$. In addition, when one of R, W and Z is —C(O)CHR$_4$CH$_2$C(O)OR$_8$, then the others cannot be the same substituent.

DETAILED DESCRIPTION OF THE INVENTION

The invention in its broadest aspects relates to pyridazinone compounds which exhibit cardiotonic activity, vasodilating activity, platelet anti-aggregatory activity and phosphodiesterase fraction III inhibitory activity. The pyridazinone compounds of the invention demonstrating these activities are shown by formula I above. The pyridazinone compounds contain a benzoxazine ring. The invention further relates to intermediates of the pyridazinone compounds.

The preferred compounds of the present invention are those wherein R$_1$ is CH$_3$, R$_2$ and R$_3$ are hydrogen, R$_4$, R$_5$ and R$_6$ are H or CH$_3$, X is O or H$_2$ and the pyridazinone ring is attached at C-7 of the benzoxazine ring.

The starting materials for preparing the compounds of the present invention can be prepared as shown in Scheme 1.

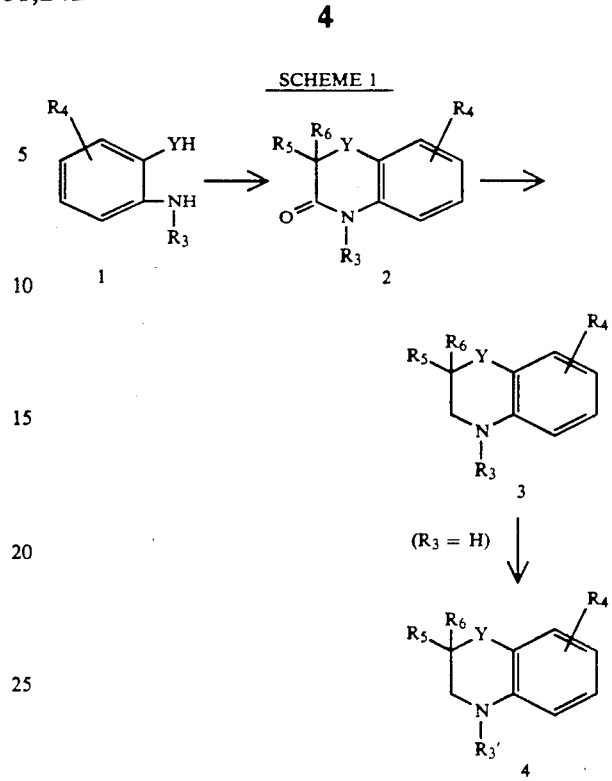

SCHEME 1 wherein R'$_3$ is RCO or RSO$_2$, wherein R is lower alkyl and the alkyl group contains 1-6 carbon atoms, and R$_4$, R$_5$ and R$_6$ are as previously defined.

The benzoxazinone or benzothiazine 2 is prepared from compound 1 by the procedure of Shridhar, *Org. Prep. Proc. Int.* 14, 195 (1982). Compound 2 is refluxed for several hours in one equivalent of diborane in tetrahydrofuran to produce the benzoxazine or benzothiazine 3. Compound 3, where R$_3$ is H, is treated with a sulfonyl or acyl compound such as methanesulfonyl chloride or acetyl chloride and pyridine in a solvent such as dichloromethane and refluxed for several hours to produce the benzoxazine or benzothiazine 4.

The compounds of formula I can be prepared as shown in Schemes 2, 3 and 4.

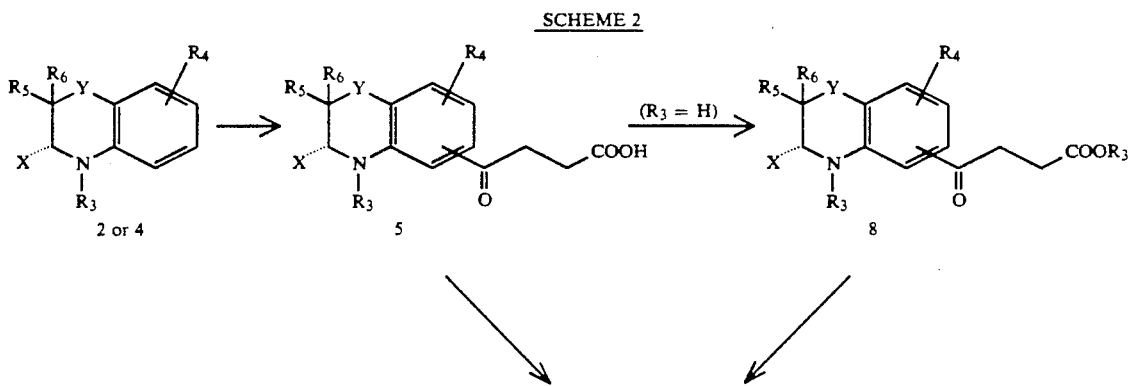

SCHEME 2

-continued
SCHEME 2

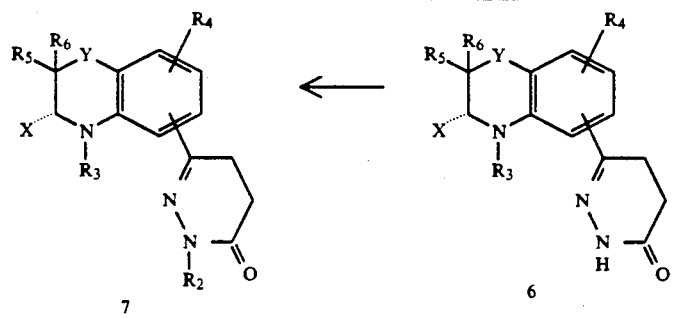

The benzoxazine or benzothiazine 2 or 4 is acylated by the method of Thyes, *J. Med. Chem.* 26, 800 (1983) using succinic anhydride to produce the compound 5. Compound 5 is refluxed for 1-8 hours with 2.2 equivalents of hydrazine in an alcohol solvent such as methanol to give compound 6. Alternatively, compound 6 can be prepared by first esterifying compound 5 in alcoholic HCl to form compound 8 and then reacting compound 8 with hydrazine. Compound 6 can be alkylated at the 2-position of the pyridazinone ring by treatment in an inert solvent such as dimethylformamide with an alkali metal base such as sodium hydride and subsequent treatment with an alkyl halide, $R_2X$ wherein $R_2$ is as defined above and X is chloro, bromo or iodo, at about 0°-40° C. for about 0.5-8 hours to give compound 7. Alternatively, compound 5 (when $R_3$ is H) can be alkylated at the 4-position as described above to give compound 8. Compound 8 is refluxed with hydrazine to produce compound 6. The N-acylated derivative 7 ($X=H_2$; $R_3$=acyl or sulfonyl) was prepared from 6 ($X=H_2$; $R_3$=H) by treatment with a base, such as triethylamine, and the appropriate acid chloride, such as acetyl chloride, methanesulfonyl chloride, benzoyl chloride, for example, as described above.

SCHEME 3

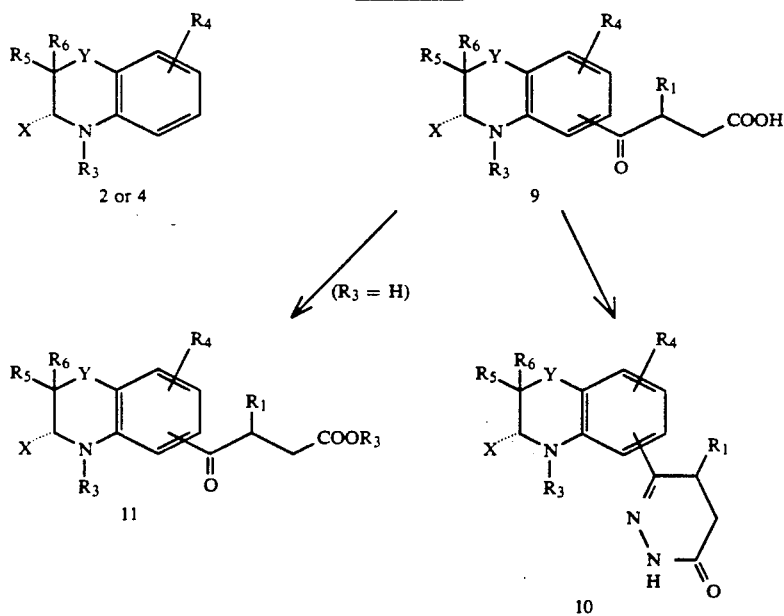

To prepare a 5-alkylated pyridazinone, the benzoxazine or benzothiazine 2 or 4 is acylated with propionyl chloride by the method of Thyes, supra, and the resulting product is converted to compound 9 by the method of McEvoy and Allen, *J. Org. Chem.* 38, 4044 (1973). Compound 9 is reacted with hydrazine or alkylated as described above to produce compounds 10 and 11, respectively. Compound 11 can be reacted with hydrazine to give compound 10. Compound 10 can be alkylated at the 2-position of the pyridazinone ring or acylated at the 4-position of the benzoxazine or benzothiazine ring as described previously.

SCHEME 4

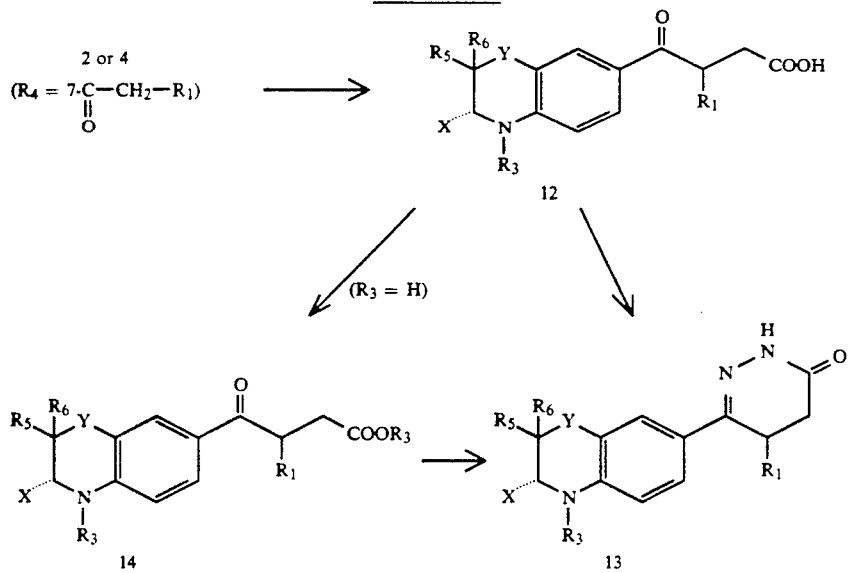

The benzoxazine or benzothiazine 2 or 4, when R₄ is

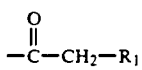

at the 7-position of the ring, is converted to compound 12 by the method of McEvoy and Allen, supra. Compound 12 is reacted with hydrazine or alkylated as described above to produce compounds 13 and 14, respectively. Compound 14 can be reacted with hydrazine to give compound 13. Compound 13 can be alkylated at the 2-position of the pyridazinone ring or acylated at the 4-position of the benzoxazine or benzothiazine ring as previously described.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included, injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 0.001 to about 10 mg/kg, and preferably from about 0.01 to about 0.1 mg/kg of the active ingredient.

The following examples describe the invention in greater particularity and are intended to be a way of illustrating but not limiting the invention.

EXAMPLE 1

3,4-Dihydro-7-(1-oxopropyl)-3-oxo-1,4(2H)-benzoxazine

4-Amino-3-hydroxypropiophenone (32 g) was dissolved in 250 ml of methyl isobutyl ketone and 250 ml of water containing 40 g of sodium bicarbonate. Chloroacetyl chloride (17 ml) was added to the rapidly stirring mixture at 0° C. The mixture was then heated at reflux for four hours. Upon cooling, the title compound was isolated by filtration and washed with ether. Yield: 35 g (88%), mp 174.5°–176° C.

The following compounds were prepared by the above procedure, using the appropriate starting materials:

3,4-dihydro-3-oxo-1,4(2H)-benzoxazine, mp 170°–171° C.;

3,4-dihydro-6-methyl-3-oxo-1,4(2H)-benzoxazine, mp 204.5°–205.5° C.;

3,4-dihydro-7-methyl-3-oxo-1,4(2H)-benzoxazine, mp 193°–195° C.;

3,4-dihydro-2-methyl-3-oxo-1,4(2H)-benzoxazine, mp 143°–145° C.;

3,4-dihydro-2,2-dimethyl-3-oxo-1,4(2H)-benzoxazine, mp 161°–163° C.;

3,4-dihydro-2,7-dimethyl-3-oxo-1,4(2H)-benzoxazine, mp 152°–153° C.;

3,4-dihydro-4-(1-methylethyl)-3-oxo-1,4(2H)-benzoxazine, oil;

3,4-dihydro-4-cyclopentyl-3-oxo-1,4(2H)-benzoxazine, oil;

3,4-dihydro-2-methyl-4-(1-methylethyl)-3-oxo-1,4(2H)-benzoxazine, oil;

3,4-dihydro-2-methyl-4-cyclopentyl-3-oxo-1,4(2H)-benzoxazine, oil; and
3,4-dihydro-7-(1-oxoethyl)-3-oxo-1,4(2H)-benzoxazine, mp 193°-196° C.

The following compounds were prepared by the above procedure, using the appropriate starting materials:
3,4-dihydro-3-oxo-1,4[2H]benzothiazine;
3,4-dihydro-3-oxo-7-(1-oxopropyl)-1,4[2H]benzothiazine;
3,4-dihydro-2-methyl-3-oxo-1,4[2H]benzothiazine; and
3,4-dihydro-2,2-dimethyl-3-oxo-1,4[2H]benzothiazine.

EXAMPLE 2

3,4-Dihydro-1,4(2H)-benzoxazine 3,4-Dihydro-3-oxo-1,4(2H)-benzoxazine was refluxed for several hours in one equivalent of diborane in tetrahydrofuran. Excess sodium hydroxide solution was added, the product was extracted with ether and the solvent was evaporated to give the title compound as an oil.

The following compounds were prepared by the above procedure, using the appropriate starting materials:
3,4-dihydro-6-methyl-1,4(2H)-benzoxazine and
3,4-dihydro-2-methyl-1,4(2H)-benzoxazine.

EXAMPLE 3

3,4-Dihydro-2,7-dimethyl-4-(1-oxoethyl)-1,4(2H)-benzoxazine 3,4-Dihydro-2,7-dimethyl-1,4(2H)-benzoxazine was dissolved in dichloromethane, and one equivalent each of acetyl chloride and triethylamine were added in that order. The mixture was refluxed for several hours, cooled and washed with water, and then with saturated NaHCO$_3$ solution. Evaporation of the organic layer provided the product, mp 60.5°-63° C.

The following compounds were prepared by the above procedure, using the appropriate starting materials:
3,4-dihydro-4-methanesulfonyl-1,4(2H)-benzoxazine, mp 74.5°-77° C.;
3,4-dihydro-4-(1-oxoethyl)-1,4(2H)-benzoxazine, oil; and
3,4-dihydro-2-methyl-4-(1-oxoethyl)-1,4(2H)-benzoxazine, mp 80°-82° C.

EXAMPLE 4

4-Oxo-4-(3,4-dihydro-2-methyl-3-oxo-1,4(2H)-benzoxazin-6-yl)butyric acid 3,4-Dihydro-2-methyl-3-oxo-1,4(2H)-benzoxazine (11.4 g) and succinic anhydride (7 g) were added to 93 g of aluminum chloride and 15.3 ml of dimethylformamide. The mixture was stirred at 70° C. for 2.5 hours and then poured onto ice, giving a solid which was collected by filtration and washed with water. Drying under vacuum gave 16.5 g of the title compound (90% yield), mp 198°-200° C.

The following compounds were prepared by the above procedure, using the appropriate starting materials:
4-oxo-4-(3,4-dihydro-3-oxo-1,4(2H)-benzoxazin-6-yl)butyric acid, mp 206°-208° C.;
4-oxo-4-(3,4-dihydro-2,2-dimethyl-3-oxo-1,4(2H)-benzoxazin-6-yl)butyric acid;
4-oxo-4-(3,4-dihydro-7-methyl-3-oxo-1,4(2H)-benzoxazin-6-yl)butyric acid, mp 226°-228° C.;
4-oxo-4-(3,4-dihydro-2,7-dimethyl-3-oxo-1,4(2H)-benzoxazin-6-yl)butyric acid;
4-oxo-4-(3,4-dihydro-4-methanesulfonyl-1,4(2H)-benzoxazin-6-yl)butyric acid, mp 184°-187° C.;
4-oxo-4-(3,4-dihydro-4-(1-oxoethyl)-1,4(2H)-benzoxazin-6-yl)butyric acid, mp 143°-144.5° C.;
4-oxo-4-(3,4-dihydro-6-methyl-3-oxo-1,4(2H)-benzoxazin-8-yl)butyric acid; and
4-oxo-4-(3,4-dihydro-6-methyl-3-oxo-1,4(2H)-benzoxazin-7-yl)butyric acid.

EXAMPLE 5

Methyl 4-oxo-4-(3,4-dihydro-4-methyl-3-oxo-1,4(2H)-benzoxazin-6-yl)butyrate 3,4-Dihydro-3-oxo-1,4(2H)-benzoxazine was alkylated by dissolving the acid in dimethylformamide and adding two equivalents of 60% sodium hydride in oil suspension. After one-half hour, two equivalents of methyl iodide were added. The mixture was stirred under nitrogen for 12 hours, then poured into water. The product was collected by extraction into ethyl acetate and evaporation of the solvent, mp 139°-140° C.

The following compounds were prepared by the above procedure, using the appropriate starting materials:
methyl 4-oxo-4-(3,4-dihydro-2,4dimethyl-3-oxo-1,4(2H)-benzoxazin-6-yl)butyrate, oil;
methyl 4-oxo-4-(3,4-dihydro-4,7-dimethyl-3-oxo-1,4(2H)-benzoxazin-6-yl)butyrate, oil;
methyl 4-oxo-4-(3,4-dihydro-2,4,7-trimethyl-3-oxo-1,4(2H)-benzoxazin-6-yl)butyrate, oil;
methyl 4-oxo-4-(3,4-dihydro-4,6-dimethyl-3-oxo-1,4(2H)-benzoxazin-8-yl)butyrate, oil;
methyl 4-oxo-4-(3,4-dihydro-4,6-dimethyl-3-oxo-1,4(2H)-benzoxazin-7-yl)butyrate, oil;
methyl 4-oxo-4-(3,4-dihydro-2,4-trimethyl-3-oxo-1,4(2H)-benzoxazin-6-yl)butyrate, oil;
methyl 4-oxo-4-(3,4-dihydro-4-methyl-3-oxo-1,4(2H)-benzoxazin-6-yl)-3-methylbutyrate, oil;
methyl 4-oxo-4-(3,4-dihydro-2,4-dimethyl-3-oxo-1,4(2H)-benzoxazin-6-yl)-3-methylbutyrate, oil;
methyl 4-oxo-4-(3,4-dihydro-4,7-dimethyl-3-oxo-1,4(2H)-benzoxazin-6-yl)-3-methylbutyrate, oil;
methyl 4-oxo-4-(3,4-dihydro-2,4,7-trimethyl-3-oxo-1,4(2H)-benzoxazin-6-yl)-3-methylbutyrate, oil;
methyl 4-oxo-4-(3,4-dihydro-4,6-dimethyl-3-oxo-1,4(2H)-benzoxazin-8-yl)-3-methylbutyrate, oil; and
methyl 4-oxo-4-(3,4-dihydro-4-methyl-3-oxo-1,4(2H)-benzoxazin-7-yl)-3-methylbutyrate, oil.

EXAMPLE 6

4-Oxo-4-(3,4-dihydro-7-methyl-3-oxo-1,4(2H)-benzoxazin-6-yl)-3-methylbutyric acid A. 3,4-Dihydro-7-methyl-3-oxo-1,4(2H)-benzoxazine was acylated with propionyl chloride by the method of Example 4 in 85% yield. The product of this operation was converted to the title compound as follows:

B. 3,4-Dihydro-7-methyl-6-(1-oxopropyl)-3-oxo-1,4(2H)-benzoxazine (23.7 g) was added to a mixture of 13 g of dimethylamine hydrochloride and 15 ml of 37% aqueous formaldehyde solution in 68 ml of acetic anhydride. After heating on a steam bath for three hours, 50 ml of acetone was added and heating was continued for 15 minutes. The solvents were removed by evaporation at reduced pressure and the residue was dissolved in 1N HCl and washed with ethyl acetate. The aqueous layer was basified with sodium hydroxide and the resultant crystals were collected by filtration. This product was dissolved in 500 ml of acetone and 10 ml of iodomethane were added. After heating at reflux overnight, the solid which formed was collected by filtration and washed with acetone. The product was dissolved in 400 ml of 50% aqueous methanol and 18 g of potassium cyanide in 200 ml of water was added. After stirring overnight at room temperature, the solid was collected and washed with water. The damp filter cake was suspended in 500 ml of 6N HCl and heated at reflux for 1.5 hours. Upon cooling a white precipitate formed which was collected by filtration and washed with water to give 19.4 g (81% yield) of the title compound, mp 169.5°–172° C.

The following compounds were prepared by the above procedure, using appropriate starting materials:
4-oxo-4-(3,4-dihydro-1,4(2H)-benzoxazin-6-yl)-3-methylbutyric acid;
4-oxo-4-(3,4-dihydro-2-methyl-1,4(2H)-benzoxazin-6-yl)-3-methylbutyric acid;
4-oxo-4-(3,4-dihydro-3-oxo-1,4(2H)-benzoxazin-6-yl)-3-methylbutyric acid;
4-oxo-4-(3,4-dihydro-2-methyl-3-oxo-1,4(2H)-benzoxazin-6-yl)-3-methylbutyric acid;
4-oxo-4-(3,4-dihydro-2,7-dimethyl-3-oxo-1,4(2H)-benzoxazin-6-yl)-3-methylbutyric acid;
4-oxo-4-(3,4-dihydro-4-(1-methylethyl)-2-methyl-3-oxo-1,4(2H)-benzoxazin-6-yl)-3-methylbutyric acid;
4-oxo-4-(3,4-dihydro-4-cyclopentyl-2-methyl-3-oxo-1,4(2H)-benzoxazin-6-yl)-3-methylbutyric acid;
4-oxo-4-(3,4-dihydro-6-methyl-3-oxo1,4(2H)-benzoxazin-8-yl)-3-methylbutyric acid; and
4-oxo-4-(3,4-dihydro-6-methyl-1,4(2H)-benzoxazin-8-yl)-3-methylbutyric acid.

EXAMPLE 7

4-Oxo-4-(3,4-dihydro-3-oxo-1,4(2H)-benzoxazin-7-yl)-3-methylbutyric acid 3,4-Dihydro-7-(1-oxopropyl)-3-oxo-1,4(2H)-benzoxazine (from Example 1) was converted to the title compound by the method of Example 6B.

EXAMPLE 8

6-(3,4-Dihydro-4-methanesulfonyl-1,4(2H)-benzoxazin-6-yl)-2,3,4,5-tetrahydropyridazin-3-one Ethyl 4-oxo-4-(3,4-dihydro-4-methanesulfonyl-1,4-(2H)-benzoxazin-6-yl)butyrate was suspended in methanol and 2.2 equivalents of hydrazine were added. The mixture was brought to reflux and stirred for 24 hours. Upon cooling, crystals of the desired product formed and were collected by filtration. Recrystallization from ethanol gave pure title compound, mp 245° C.

Theor. $C_{13}H_{15}N_3O_4S$: C, 50.47; H, 4.90; N, 13.59. Found: C, 50.46; H, 4.85; N, 13.67.

When in the above procedure, ethyl 4-oxo-4-(3,4-dihydro-4-methanesulfonyl-1,4(2H)-benzoxazin-6-yl)-3-ethylbutyrate; ethyl 4-oxo-4-(3,4-dihydro-4-methanesulfonyl-1,4(2H)-benzoxazin-6-yl)-3-hexylbutyrate; or ethyl 4-oxo-4-(3,4-dihydro-4-methanesulfonyl-1,4(2H)-benzoxazin-6-yl)-3-(1-methylethyl)butyrate is utilized as the starting material, the corresponding 5-ethyl-, 5-hexyl- or -5-(1-methylethyl)-pyridazin-3-one derivative is obtained.

EXAMPLE 9

6-(3,4-Dihydro-4-methanesulfonyl-1,4(2H)-benzoxazin-6-yl)-2,3,4,5-tetrahydro-2-methylpyridazin-3-one 6-(3,4-Dihydro-4-methanesulfonyl-1,4(2H)-benzoxazin-6-yl)-2,3,4,5-tetrahydropyridazin-3-one (3 g) was suspended in 50 ml of dimethylformamide and one equivalent of 60% sodium hydride in oil was added. When gas evolution ceased, one equivalent of methyl iodide was added and the mixture allowed to stand for 1.5 hours followed by one hour at 40° C. The mixture was cooled and then poured into 200 ml of ice water, giving a precipitate that was collected by filtration, washed with water and recrystallized from ethanol. The material was further purified by chromatography on silica gel eluted with 1:1 EtOAc:Et$_2$O yielding 0.97 g of the title product, mp 162°–165° C.

Theor. $C_{14}H_{17}N_3O_4S$: C, 51.99; H, 5.31; N, 13.00. Found: C, 51.92; H, 5.32; N, 12.96.

EXAMPLE 10

6-(3,4-Dihydro-4-methanesulfonyl-1,4(2H)-benzoxazin-6-yl)-2,3,4,5-tetrahydro-2-pentylpyridazin-3-one 6-(3,4-Dihydro-4-methanesulfonyl-1,4(2H)-benzoxazin-6-yl)-2,3,4,5-tetrahydropyridazin-3-one was reacted with pentyl bromide in place of methyl iodide following the procedure of Example 9. The title compound was recovered, yield 1.46 g, mp 138°–139° C.

Theor. $C_{18}H_{25}N_3O_4S$: C, 56.96; H, 6.65; N, 11.07. Found: C, 56.67; H, 6.49; N, 11.05.

When in the above procedure, bromocyclohexane or 2-bromopropane is utilized in place of pentyl bromide, the corresponding 2-cyclohexyl or 2-(1-methylethyl)-pyridazinone is obtained.

EXAMPLE 11

6-(3,4-Dihydro-4-methanesulfonyl-1,4(2H)-benzoxazin-6-yl)-2,3,4,5-tetrahydro-2-(2-propenyl)pyridazin-3-one 6-(3,4-Dihydro-4-methanesulfonyl-1,4(2H)-benzoxazin-6-yl)-2,3,4,5-tetrahydropyridazin-3-one was reacted with allyl bromide instead of methyl iodide, following the procedure of Example 9. The title compound was recovered, yield 2.03 g, mp 153°–155° C.

Theor. $C_{16}H_{19}N_3O_4S$: C, 54.99; H, 5.49; N, 12.03. Found: C, 54.94; H, 5.58; N, 11.92.

EXAMPLE 12

6-(3,4-Dihydro-1,4(2H)-benzoxazin-6-yl)-2,3,4,5-tetrahydropyridazin-3-one

The method of Example 8 was followed using 4-oxo-4-(3,4-dihydro-1,4-(2H)-benzoxazin-6-yl)butyric acid as the starting material to give the title compound in 60% yield, mp 198°–199° C.

Theor. $C_{12}H_{13}N_3O_2$: C, 62.31; H, 5.68; N, 18.17. Found: C, 62.35; H, 5.72; N, 18.18.

EXAMPLE 13

6-(4-Acetyl-3,4-dihydro-1,4(2H)-benzoxazin-6-yl)-2,3,4,5-tetrahydropyridazin-3-one The method of Example 8 was followed using 4-oxo-4-(3,4-dihydro-3,4-acetyl-1,4(2H)-benzoxazin-6-yl)butyric acid as the starting material to yield the title compound in 40% yield, mp 156°–158° C.

Theor. $C_{14}H_{15}N_3O_3$: C, 61.52; H, 5.54; N, 15.38. Found: C, 61.49; H, 5.55; N, 15.24.

EXAMPLE 14

6-(3,4-Dihydro-4-(3,4-dimethoxyphenylcarbonyl)-1,4(2H)-benzoxazin-6-yl)-2,3,4,5-tetrahydropyridazin-3-one 6-(3,4-Dihydro-1,4(2H)-benzoxazin-6-yl)-2,3,4,5-tetrahydropyridazin-3-one was dissolved in methylene chloride and 1.1 equivalent of triethylamine. 1.1 equivalent of 3,4-dimethoxybenzoylchloride was added and the mixture heated at reflux for four hours. The solution was washed with sodium bicarbonate solution and then evaporated to dryness. The residue was chromatographed on silica gel eluting with 1:1 ethyl acetate:ethyl ether. The title compound was collected as white needles, mp 207°–208° C.

Theor. $C_{21}H_{21}N_3O_5$: C, 63.78; H, 5.36; N, 10.63. Found: C, 63.78; H, 5.40; N, 10.64.

EXAMPLE 15

6-(3,4-Dihydro-1,4(2H)-benzoxazin-6-yl)-2,3,4,5-tetrahydro-5-methylpyridazin-3-one The method of Example 8 was followed using 4-oxo-4-(3,4-dihydro-1,4(2H)-benzoxazin-6-yl)-3-methylbutyric acid as the starting material to produce the title compound, mp 166°–168° C.

Theor. $C_{13}H_{15}N_3O_2$: C, 63.65; H, 6.18; N, 17.13. Found: C, 63.47; H, 6.22; N, 16.90.

When in the above procedure, 4-oxo-4-(3,4-dihydro-1,4(2H)-benzoxazin-6-yl)-3-ethylbutyric acid; 4-oxo-4-(3,4-dihydro-1,4(2H)-benzoxazin-6-yl)-3-hexylbutyric acid or 4-oxo-4-(3,4-dihydro-1,4(2H)-benzoxazin-6-yl)-3-(1-methylethyl)butyric acid is utilized, the corresponding 5-ethyl-, 5-hexyl- or -5-(1-methylethyl)-pyridazin-3-one derivative is obtained.

EXAMPLE 16

6-(4-Acetyl-3,4-dihydro-1,4(2H)-benzoxazin-6-yl)-2,3,4,5-tetrahydro-5-methylpyridazin-3-one 6-(3,4-Dihydro-1,4(2H)-benzoxazin-6-yl)-2,3,4,5-tetrahydro-5-methylpyridazin-3-one was suspended in tetrahydrofuran and one equivalent of acetyl chloride was added. After one half hour at 0° C., the solvent was removed in vacuo, and the product was crystallized from ethanol in 61% yield, mp 185.5°–186° C.

Theor. $C_{15}H_{17}N_3O_3$: C, 62.69; H, 5.97; N, 14.63. Found: C, 62.85; H, 6.03; N, 14.64.

EXAMPLE 17

6-(3,4-Dihydro-4-methanesulfonyl-1,4(2H)-benzoxazin-6-yl)-2,3,4,5-tetrahydro-5-methylpyridazin-3-one The method of Example 16 was followed using methanesulfonyl chloride instead of acetyl chloride. Pyridine was added to the mixture. After one hour at 0° C., the mixture was warmed to room temperature and allowed to stir for 48 hours and then refluxed for 24 hours. Acetonitrile was added and the mixture was adsorbed onto silica gel and eluted with ethyl acetate. The title compound was crystallized from ethanol to give a 25% yield, mp 207°–212° C.

Theor. $C_{14}H_{17}N_3O_4S$: C, 51.99; H, 5.31; N, 13.00. Found: C, 52.42; H, 5.31; N, 13.39.

EXAMPLE 18

6-(3,4-Dihydro-2-methyl-1,4(2H)-benzoxazin-6-yl)-2,3,4,5-tetrahydropyridazin-3-one The method of Example 8 was followed using 4-oxo-4-(3,4-dihydro-2-methyl-1,4(2H)benzoxazin-6-yl)butyric acid as the starting material to give the desired product in 10% yield, mp 294.5°–295.5° C.

Theor. $C_{13}H_{15}N_3O_2$: C, 63.65; H, 6.18; N, 17.13. Found: C, 63.37; H, 6.16; N, 17.41.

When in the above procedure, 4-oxo-4-(3,4-dihydro-2-methyl-7-pentyl-1,4(2H)-benzoxazin-6-yl)butyric acid; 4-oxo-4-(3,4-dihydro-2-hexyl-7-isopropyl-1,4(2H)-benzoxazin-6-yl)-2-hexylbutyric acid; 4-oxo-4-(3,4-dihydro-2-methyl-7-cyclohexyl-1,4(2H)-benzoxazin-6-yl)butyric acid; 4-oxo-4-(3,4-dihydro-2-isobutyl-7-methoxy-1,4(2H)-benzoxazin-6-yl)butyric acid or 4-oxo-4-(3,4-dihydro-2-cyclopentyl-1,4(2H)-benzoxazin-6-yl)butyric acid is used, the corresponding pyridazinone derivative is obtained.

EXAMPLE 19

6-(3,4-Dihydro-2-methyl-1,4(2H)-benzoxazin-6-yl)-2,3,4,5-tetrahydro-5-methylpyridazin-3-one The method of Example 8 was followed using 4-oxo-4-(3,4-dihydro-2-methyl-1,4(2H)benzoxazin-6-yl)-3-methylbutyric acid as the starting material. The product was further purified by chromatography on silica gel, mp 179°–182° C.

Theor. $C_{14}H_{17}N_3O_2$: C, 64.83; H, 6.62; N, 16.21. Found: C, 64.51; H, 6.64; N, 15.84.

When in the above procedure, 4-oxo-4-(3,4-dihydro-2-methyl-1,4(2H)-benzoxazin-6-yl)-3-ethylbutyric acid; 4-oxo-4-(3,4-dihydro-2-methyl-1,4(2H)benzoxazin-6-yl)-3-hexylbutyric acid or 4-oxo-4-(3,4-dihydro-2-methyl-1,4(2H)benzoxazin-6-yl)-3-(1-methylethyl)butyric acid is utilized, the corresponding 5-ethyl-, 5-hexyl- or -5-(1-methylethyl)-pyridizin-3-one derivative is obtained.

EXAMPLE 20

6-(3,4-Dihydro-3-oxo-1,4(2H)-benzoxazin-6-yl)-2,3,4,5-tetrahydropyridazin-3-one

Following the method of Example 8, but using methyl 4-oxo-4-(3,4-dihydro-3-oxo-1,4(2H)benzoxazin-6-yl)butyrate, the title compound was obtained and was recrystallized from ethanol and then from acetonitrile as a hydrate, mp 274°–275° C.

Theor. $C_{12}H_{11}N_3O_3 \cdot H_2O$: C, 57.70; H, 4.65; N, 16.83. Found: C, 57.54; H, 4.50; N, 16.79.

EXAMPLE 21

6-(3,4-Dihydro-4-methyl-3-oxo-1,4(2H)-benzoxazin-6-yl)-2,3,4,5-tetrahydropyridazin-3-one The method of Example 8 was followed using methyl 4-oxo-4-(3,4-dihydro-4-methyl-3-oxo-1,4(2H)benzoxazin-6-yl)butyrate as the starting material. The product was purified by column chromatography followed by several recrystallizations from acetonitrile, mp 247°–247.5° C.

Theor. $C_{13}H_{13}N_3O_3$: C, 60.21; H, 5.06; N, 16.21. Found: C, 59.85; H, 4.98; N, 16.26.

EXAMPLE 22

6-(3,4-Dihydro-3-oxo-1,4(2H)-benzoxazin-6-yl)-2,3,4,5-tetrahydro-5-methylpyridazin-3-one The method of Example 8 was followed using methyl 4-oxo-4-(3,4-dihydro-3-oxo-1,4(2H)benzoxazin-6-yl)-3-methylbutyrate as the starting material. The product was purified by crystallization from acetonitrile, followed by column chromatography on silica gel and eluted with 5% methanol in dichloromethane, mp 265°-267° C.

Theor. $C_{13}H_{13}N_3O_3 \cdot \frac{1}{4} H_2O$: C, 59.19; H, 5.17; N, 15.93. Found: C, 59.22; H, 4.98; N, 15.92.

When in the above procedure, 4-oxo-4-(3,4-dihydro-3-oxo-1,4(2H)-benzoxazin-6-yl)-3-ethylbutyrate; 4-oxo-4-(3,4-dihydro-3-oxo-1,4(2H)-benzoxazin-6-yl)-3-hexylbutyrate or 4-oxo-4-(3,4-dihydro-3-oxo-1,4(2H)benzoxazin-6-yl)-3-(1-methylethyl)butyrate is utilized, the corresponding 5-ethyl-, 5-hexyl- or -5-(1-methylethyl)-pyridazin-3-one derivative is obtained.

EXAMPLE 23

6-(3,4-Dihydro-4-methyl-3-oxo-1,4(2H)-benzoxazin-6-yl)-2,3,4,5-tetrahydro-5-methylpyridazin-3-one The method of Example 8 was followed using methyl 4-oxo-4-(3,4-dihydro-4-methyl-3-oxo-1,4(2H)benzoxazin-6-yl)-3-methylbutyrate as the starting material. The product was purified by chromatography and eluted with 5% methanol in dichloromethane, mp 215°-218° C.

Theor. $C_{14}H_{14}N_3O_3$: C, 61.52; H, 5.54; N, 15.34. Found: C, 61.80; H, 5.75; N, 15.63.

EXAMPLE 24

6-(3,4-Dihydro-2-methyl-3-oxo-1,4(2H)-benzoxazin-6-yl)-2,3,4,5-tetrahydropyridazin-3-one The method of Example 8 was followed using 4-oxo-4-(3,4-dihydro-2-methyl-3-oxo-1,4(2H)-benzoxazin-6-yl)butyric acid as the starting material, to produce the title compound in 75% yield, mp 275°-276° C.

Theor. $C_{13}H_{13}N_3O_3$: C, 60.21; H, 5.06; N, 16.21. Found: C, 60.02; H, 5.22; N, 16.08.

EXAMPLE 25

6-(3,4-Dihydro-2,4-dimethyl-3-oxo-1,4(2H)-benzoxazin-6-yl)-2,3,4,5-tetrahydropyridazin-3-one The title compound was produced in 25% yield, by following the method of Example 8, using methyl-4-oxo-4-(3,4-dihydro-2,4-dimethyl-3-oxo-1,4(2H)-benzoxazin-6-yl)butyrate as the starting material, mp 210°-211° C.

Theor. $C_{14}H_{15}N_3O_3 \cdot \frac{1}{4} H_2O$: C, 59.56; H, 5.72; N, 15.16. Found: C, 59.93; H, 5.48; N, 15.16.

EXAMPLE 26

6-(3,4-Dihydro-2-methyl-3-oxo-1,4(2H)-benzoxazin-6-yl)-2,3,4,5-tetrahydro-5-methylpyridazin-3-one The method of Example 8 was followed using 4-oxo-4-(3,4-dihydro-2-methyl-3-oxo-1,4(2H)-benzoxazin-6-yl)-3-methylbutyric acid as the starting material, to yield the title compound in 50% yield, mp 271°-272° C.

Theor. $C_{14}H_{15}N_3O_3$: C, 61.52; H, 5.54; N, 15.38. Found: C, 61.34; H, 5.59; N, 15.41.

When in the above procedure, 4-oxo-4-(3,4-dihydro-2-methyl-7-pentyl-3-oxo-1,4(2H)-benzoxazin-6-yl)butyric acid; 4-oxo-4-(3,4-dihydro-2-hexyl-7-isopropyl-3-oxo-1,4(2H)-benzoxazin-6-yl)-butyric acid; 4-oxo-4-(3,4-dihydro-2-methyl-7-cyclohexyl-3-oxo-1,4(2H)-benzoxazin-6-yl)butyric acid; 4-oxo-4-(3,4-dihydro-2-isobutyl-7-methoxy-1,4(2H)-benzoxazin-6-yl)butyric acid or 4-oxo-4-(3,4-dihydro-2-cyclopentyl-3-oxo-1,4(2H)-benzoxazin-6-yl)butyric acid is used, the corresponding pyridazinone derivative is obtained.

EXAMPLE 27

6-(3,4-Dihydro-2,4-dimethyl-3-oxo-1,4(2H)-benzoxazin-6-yl)-2,3,4,5-tetrahydro-5-methylpyridazin-3-one Following the method of Example 8, using methyl 4-oxo-4-(3,4-dihydro-2,4-dimethyl-3-oxo-1,4(2H)-benzoxazin-6-yl)-3-methylbutyrate as the starting material, the title compound was obtained, in 40% yield, mp 184°-185° C.

Theor. $C_{15}H_{17}N_3O_3$: C, 62.70; H, 5.98; N, 14.63. Found: C, 62.75; H, 5.95; N, 14.79.

EXAMPLE 28

6-(3,4-Dihydro-7-methyl-3-oxo-1,4(2H)-benzoxazin-6-yl)-2,3,4,5-tetrahydropyridazin-3-one The method of Example 8 was followed, using 4-oxo-4-(3,4-dihydro-7-methyl-3-oxo-1,4(2H)-benzoxazin-6-yl)butyric acid as the starting material, to produce the title compound in 55% yield, mp 255°-257° C.

Theor. $C_{13}H_{13}N_3O_3$: C, 60.21; H, 5.06; N, 16.21. Found: C, 59.90; H, 5.26; N, 15.95.

When in the above procedure, 4-oxo-4-(3,4-dihydro-7-pentyl-3-oxo-1,4(2H)-benzoxazin-6-yl)butyric acid; 4-oxo-4-(3,4-dihydro-2-hexyl-7-isopropyl-3-oxo-1,4(2H)-benzoxazin-6-yl)butyric acid; 4-oxo-4-(3,4-dihydro-7-cyclohexyl-3-oxo-1,4(2H)-benzoxazin-6-yl)-butyric acid; 4-oxo-4-(3,4-dihydro-2-isobutyl-7-methoxy-3-oxo-1,4(2H)benzoxazin-6-yl)butyric acid or 4-oxo-4-(3,4-dihydro-2-cyclopentyl-3-oxo-1,4(2H)-benzoxazin-6-yl)butyric acid is used, the corresponding pyridazinone derivative is obtained.

EXAMPLE 29

6-(3,4-Dihydro-4,7-dimethyl-3-oxo-1,4(2H)-benzoxazin-6-yl)-2,3,4,5-tetrahydropyridazin-3-one The title compound was obtained, in 47% yield, by following the method of Example 8, using methyl 4-oxo-4-(3,4-dihydro-4,7-dimethyl-3-oxo-1,4(2H)-benzoxazin-6-yl)butyrate as the starting material, mp 227°-228.5° C.

Theor. $C_{14}H_{15}N_3O_3$: C, 61.52; H, 5.54; N, 15.38. Found: C, 61.65; H, 5.57; N, 15.26.

EXAMPLE 30

6-(3,4-Dihydro-7-methyl-3-oxo-1,4(2H)-benzoxazin-6-yl)-2,3,4,5-tetrahydro-5-methylpyridazin-3-one The method of Example 8 was followed, using 4-oxo-4-(3,4-dihydro-7-methyl-3-oxo-1,4(2H)-benzoxazin-6-yl)-3-methylbutyric acid as the starting material, to give the title compound in 51% yield, mp 163°-166° C.

Theor. $C_{14}H_{15}N_3O_3 \cdot \frac{1}{4} H_2O$: C, 60.52; H, 5.63; N, 15.13. Found: C, 60.65; H, 5.62; N, 15.03.

EXAMPLE 31

6-(3,4-Dihydro-4,7-dimethyl-3-oxo-1,4(2H)-benzoxazin-6-yl)-2,3,4,5-tetrahydro-5-methylpyridazin-3-one Following the method of Example 8, using 4-oxo-4-(3,4-dihydro-4,7-dimethyl-3-oxo-1,4(2H)-benzoxazin-6- yl)-3-methylbutyrate as the starting material, the title compound was produced, mp 180°-182° C.

Theor. $C_{15}H_{17}N_3O_3$: C, 62.70; H, 5.98; N, 14.63. Found: C, 62.77; H, 6.06; N, 14.57.

EXAMPLE 32

6-(3,4-Dihydro-2,7-dimethyl-3-oxo-1,4(2H)-benzoxazin-6-yl)-2,3,4,5-tetrahydropyridazin-3-one The method of Example 8 was followed, using 4-oxo-4-(3,4-dihydro-2,7-dimethyl-3-oxo-1,4(2H)-benzoxazin-6-yl)butyric acid to give the title compound, mp 252°-254° C.

Theor. $C_{14}H_{15}N_3O_3 \cdot \frac{1}{4} H_2O$: C, 60.52; H, 5.64; N, 15.13. Found: C, 60.50; H, 5.45; N, 15.63.

EXAMPLE 33

6-(3,4-Dihydro-2,4,7-trimethyl-3-oxo-1,4(2H)-benzoxazin-6-yl)-2,3,4,5-tetrahydropyridazin-3-one Following the method of Example 8, using methyl 4-oxo-4-(3,4-dihydro-2,4,7-trimethyl-3-oxo-1,4(2H)-benzoxazin-6-yl)butyrate as the starting material, the title compound was obtained, mp 210°-212° C.

Theor. $C_{15}H_{17}N_3O_3$: C, 62.70; H, 5.98; N, 14.63. Found: C, 62.85; H, 6.11; N, 14.93.

EXAMPLE 34

6-(3,4-Dihydro-2,7-dimethyl-3-oxo-1,4(2H)-benzoxazin-6-yl)-2,3,4,5-tetrahydro-5-methylpyridazin-3-one The method of Example 8 was followed, using 4-oxo-4-(3,4-dihydro-2,7-dimethyl-3-oxo-1,4(2H)-benzoxazin-6-yl)-3-methylbutyric acid, to yield the title compound, mp 190°-191° C.

Theor. $C_{15}H_{17}N_3O_3 \cdot \frac{1}{2} H_2O$: C, 60.80; H, 6.14; N, 14.18. Found: C, 61.18; H, 6.42; N, 13.78.

EXAMPLE 35

6-(3,4-Dihydro-2,4,7-trimethyl-3-oxo-1,4(2H)-benzoxazin-6-yl)-2,3,4,5-tetrahydro-5-methylpyridazin-3-one Following the method of Example 8, using methyl 4-oxo-4-(3,4-dihydro-2,4,7-trimethyl-3-oxo-1,4(2H)-benzoxazin-6-yl)-3-methylbutyrate as the starting material, the title compound was produced, mp 190°-192° C.

Theor. $C_{16}H_{19}N_3O_3 \cdot \frac{1}{2} H_2O$: C, 61.91; H, 6.51; N, 13.54. Found: C, 62.02; H, 6.52; N, 13.86.

When in the above procedure, 4-oxo-4-(3,4-dihydro-2,4-dimethyl-7-pentyl-3-oxo-1,4(2H)-benzoxazin-6-yl)-3-methylbutyrate; 4-oxo-4-(3,4-dihydro-2-hexyl-4-methyl-7-isopropyl-3-oxo-1,4-(2H)-benzoxazin-6-yl)-3-methylbutyrate; 4-oxo-(3,4-dihydro-2,4-dimethyl-7-cyclohexyl-3-oxo-1,4(2H)-benzoxazin-6-yl)-3-methylbutyrate; 4-oxo-4-(3,4-dihydro-2-isobutyl-4-methyl-7-methoxy-3-oxo-1,4(2H)benzoxazin-6-yl)-3-methylbutyrate; or 4-oxo-4-(3,4-dihydro-2-cyclopentyl-4,7-dimethyl-3-oxo-1,4(2H)-benzoxazin-6-yl)-3-methylbutyrate is used, the corresponding pyridazinone derivative is obtained.

EXAMPLE 36

6-(3,4-Dihydro-2-methyl-4-(1-methylethyl)-3-oxo-1,4(2H)-benzoxazin-6-yl)-2,3,4,5-tetrahydro-5-methylpyridazin-3-one The method of Example 8 was followed, using 4-oxo-4-(3,4-dihydro-4-(1-methylethyl)-3-oxo-1,4(2H)-benzoxazin-6-yl)-3-methylbutyric acid as the starting material to give the title compound, mp 204°-205° C.

Theor. $C_{17}H_{21}N_3O_3$: C, 64.73; H, 6.72; N, 13.33. Found: C, 64.67; H, 6.66; N, 13.42.

EXAMPLE 37

6-(3,4-Dihydro-4-cyclopentyl-2-methyl-3-oxo-1,4(2H)-benzoxazin-6-yl)-2,3,4,5-tetrahydro-5-methylpyridazin-3-one Following the method of Example 8, using 4-oxo-4-(3,4-dihydro-4-cyclopentyl-2-methyl-3-oxo-1,4(2H)-benzoxazin-6-yl)-3-methylbutyric acid as the starting material, the title compound was obtained, mp 220°-223° C.

Theor. $C_{19}H_{23}N_3O_3$: C, 66.84; H, 6.80; N, 12.31. Found: C, 64.61; H, 6.78; N, 12.29.

EXAMPLE 38

6-(3,4-Dihydro-6-methyl-3-oxo-1,4(2H)-benzoxazin-8-yl)-2,3,4,5-tetrahydropyridazin-3-one The method of Example 8 was followed, using 4-oxo-4-(3,4-dihydro-6-methyl-3-oxo-1,4(2H)-benzoxazin-8-yl)butyric acid as the starting material to give the title compound, mp 266°-270° C.

Theor. $C_{13}H_{13}N_3O_3$: C, 60.21; H, 5.06; N, 16.21. Found: C, 60.13; H, 5.26; N, 16.28.

EXAMPLE 39

6-(3,4-Dihydro-4,6-dimethyl-3-oxo-1,4(2H)-benzoxazin-8-yl)-2,3,4,5-tetrahydropyridazin-3-one Following the method of Example 8, using 4-oxo-4-(3,4-dihydro-4,6-dimethyl-3-oxo-1,4(2H)-benzoxazin-8-yl)butyrate as the starting material, the title compound was obtained in 16% yield, mp 266°-270° C.

Theor. $C_{14}H_{15}N_3O_3$: C, 61.52; H, 5.54; N, 15.38. Found: C, 61.18; H, 5.64; N, 15.36.

EXAMPLE 40

6-(3,4-Dihydro-6-methyl-3-oxo-1,4(2H)-benzoxazin-8-yl)-2,3,4,5-tetrahydro-5-methylpyridazin-3-one The method of Example 8 was followed, using 4-oxo-4-(3,4-dihydro-6-methyl-3-oxo-1,4(2H)-benzoxazin-8-yl)butyric acid as the starting material, to give the title compound in 31% yield, mp 252°-253.5° C.

Theor. $C_{14}H_{15}N_3O_3$: C, 61.52; H, 5.54; N, 15.38. Found: C, 61.11; H, 5.68; N, 15.26.

EXAMPLE 41

6-(3,4-Dihydro-4,6-dimethyl-3-oxo-1,4(2H)-benzoxazin-8-yl)-2,3,4,5-tetrahydro-5-methylpyridan-3-one The method of Example 8 was followed, using methyl 4-oxo-4-(3,4-dihydro-4,6-dimethyl-3-oxo-1,4(2H)-benzoxazin-8-yl)-3-methylbutyrate as the starting material, to produce the title compound in 15% yield after column chromatography on silica gel eluted with 5% methanol in dichloromethane, mp 212°-213° C.

Theor. $C_{15}H_{17}N_3O_3$: C, 62.69; H, 5.98; N, 14.63. Found: C, 62.27; H, 5.92; N, 14.57.

EXAMPLE 42

6-(3,4-Dihydro-6-methyl-1,4(2H)-benzoxazin-8-yl)-2,3,4,5-tetrahydro-5-methylpyridazin-3-one Following the method of Example 8, using ethyl 4-oxo-4-(3,4-dihydro-6-methyl-1,4(2H)-benzoxazin-8-yl)-3-methylbutyrate as the starting material, the title compound was prepared in 60% yield, mp 160°-162° C.

Theor. $C_{14}H_{17}N_3O_3$: C, 64.83; H, 6.62; N, 16.21. Found: C, 64.87; H, 6.66; N, 16.31.

When in the above procedure, 4-oxo-4-(3,4-dihydro-6-methyl-1,4(2H)-benzoxazin-8-yl)-3-ethylbutyrate; 4-oxo-4-(3,4-dihydro-6-methyl-1,4(2H)-benzoxazin-8-yl)-3-hexylbutyrate or 4-oxo-4-(3,4-dihydro-6-methyl-1,4(2H)-benzosazin-8-yl)-3-(1-methylethyl)butyrate is utilized, the corresponding 5-ethyl-, 5-hexyl- or -5-(1-methylethyl)-pyridazin-3-one derivative is obtained.

EXAMPLE 43

6-(3,4-Dihydro-4,6-dimethyl-3-oxo-1,4(2H)-benzoxazin-7-yl)-2,3,4,5-tetrahydropyridazin-3-one The method of Example 8 was followed, using methyl 4-oxo-4-(3,4-dihydro-4,6-dimethyl-3-oxo-1,4(2H)-benzoxazin-7-yl)butyrate as the starting material to produce the title compound, mp 211°–213° C.

Theor. $C_{14}H_{15}N_3O_3$: C, 61.52; H, 5.54; N, 15.38. Found: C, 61.57; H, 5.49; N, 15.28.

EXAMPLE 44

6-(3,4-Dihydro-2,2-dimethyl-3-oxo-1,4(2H)-benzoxazin-6yl)-2,3,4,5-tetrahydropyridazin-3-one The method of Example 8 was followed, using 4-oxo-4-(3,4-dihydro-2,2-dimethyl-3-oxo-1,4(2H)-benzoxazin-6-yl)butyric acid as the starting material, to give the title compound, mp 251°–254° C.

Theor. $C_{14}H_{15}N_3O_3$: C, 61.52; H, 5.54; N, 15.38. Found: C, 61.40; H, 5.58; N, 15.74.

EXAMPLE 45

6-(3,4-Dihydro-2,2,4-trimethyl-3-oxo-1,4(2H)-benzoxazin-6-yl)-2,3,4,5-tetrahydropyridazin-3-one Following the method of Example 8, using methyl 4-oxo-4-(3,4-dihydro-2,2,4-trimethyl-3-oxo-1,4(2H)-benzoxazin-6-yl)butyrate, the title compound was produced, mp 169°–171° C.

Theor. $C_{15}H_{17}N_3O_3$ C, 62.69; H, 5.98; N, 14.63. Found: C, 62.79; H, 5.86; N, 14.40.

EXAMPLE 46

6-(3,4-Dihydro-3-oxo-1,4(2H)-benzoxazin-7-yl)-2,3,4,5-tetrahydro-5-methylpyridazin-3-one The method of Example 8 was followed, using 4-oxo-4-(3,4-dihydro-3-oxo-1,4(2H)-benzoxazin-7-yl)-3-methylbutyric acid as the starting material. The title compound was obtained and recrystallized from dimethylformamide-water, then ethanol, mp >300° C.

Theor. $C_{13}H_{13}N_3O_3.\frac{1}{2}H_2O$: C, 59.18; H, 5.17; N, 15.93. Found: C, 58.88; H, 5.04; N, 16.03.

When in the above procedure, 4-oxo-4-(3,4-dihydro-3-oxo-1,4(2H)-benzoxazin-7-yl-3-ethylbutyrate; 4-oxo-4-(3,4-dihydro-3-oxo-1,4(2H)-benzoxazin-7-yl)-3-hexylbutyrate or 4-oxo-4-(3,4-dihydro-3-oxo-1,4(2H)-benzoxazin-7-yl)-3-(1-methylethyl)butyrate is utilized, the corresponding 5-ethyl-, 5-hexyl- or -5-(1-methylethyl)-pyridazin-3-one derivative is obtained.

EXAMPLE 47

6-(3,4-Dihydro-4-methyl-3-oxo-1,4(2H)-benzoxazin-7-yl)-2,3,4,5-tetrahydro-5-methylpyridazin-3-one The method of Example 8 was followed, using methyl 4-oxo-4-(3,4-dihydro-4-methyl-3-oxo-1,4(2H)-benzoxazin-7-yl)-3-methylbutyrate. The product was purified by chromatography on silica gel eluted with 5% $CH_3OH$ in $CH_2Cl_2$, mp 188°–190° C.

Theor. $C_{14}H_{15}N_3O_3$: C, 61.52; H, 5.54; N, 15.38. Found: C, 61.45; H, 5.68; N, 15.15.

EXAMPLE 48

6-(3,4-Dihydro-2-methyl-3-oxo-1,4(2H)-benzoxazin-7-yl)-2,3,4,5-tetrahydropyridazin-3-one The method of Example 8 was followed, using 4-oxo-4-(3,4-dihydro-2-methyl-3-oxo-1,4(2H)-benzoxazin-7-yl)butyric acid. The product was purified by column chromatography on silica gel eluted with 5% $CH_3OH$ in $CH_2Cl_2$. Trituration with water gave the product as a hydrate, mp 294°–295° C.

Theor. $C_{13}H_{13}N_3O_3.\frac{1}{4}H_2O$: C, 59.18; H, 5.15; N, 15.93. Found: C, 59.15; H, 4.93; N, 15.83.

The corresponding 2-alkyl-pyridazinone derivatives of the compounds prepared in any of the preceding examples are prepared in accordance with the procedures of Examples 9 and 10. The corresponding 4-acyl, 4-arylacyl or 4-alkane sulfonylbenzoxazinyl derivatives of the compounds prepared in the preceding examples where $R_3=H$ are prepared in accordance with the procedures of Examples 14, 16 and 17.

EXAMPLE 49

4-(3,4-Dihydro-3-oxo-1,4[2H]-benzothiazin-6-yl)-4-oxobutyric acid

To 100 g of aluminum chloride was added 15.6 ml of dimethylformamide. To the hot slurry was added an intimate mixture of 17 g of 3,4-dihydro-3-oxo-1,4[2H]-benzothiazine and 10 g of succinic anhydride. After 15 minutes at 75° C., the mixture was poured into 600 ml of ice and the precipitate collected by filtration and washed with water then acetone to give 20 g (73% yield) of named compound decomposing at 215°–218° C.

Theor. $C_{12}H_{11}NO_4S.\frac{1}{2}H_2O$: C, 52.54; H, 4.42; N, 5.11. Found: C, 52.54; H, 4.20; N, 5.18.

The following compounds are prepared by the above procedure, using the appropriate starting materials:
4-(3,4-dihydro-2-methyl-3-oxo-1,4[2H]-benzothiazin-6-yl-oxobutyric acid, and
4-(3,4-dihydro-2,2-dimethyl-3-oxo-1,4[2H]-benzothiazin-6-yl-oxobutyric acid.

EXAMPLE 50

Methyl 4-(3,4-dihydro-4-methyl-3-oxo-1,4[2H]-benzothiazin-6-yl)-4-oxobutyrate 4-(3,4-Dihydro-3-oxo-1,4[2H]-benzothiazin-6-yl)-4-oxobutyric acid (3 g) was suspended in 50 ml of dimethylformamide and 2.2 equivalents of 60% sodium hydride (1.0 g) were added. After 30 minutes at room temperature, 2.2 equivalents of methyl iodide (3.5 g) were added and the mixture stirred overnight. The mixture was poured into ice water and the precipitate collected by filtration. The solid was characterized by 1H NMR and used in the next reaction (see Example 54).

The following compounds are prepared by the above procedure, using the appropriate starting materials:
Methyl 4-(3,4-dihydro-2-methyl-3-oxo-1,4[2H]-benzothiazin-6-yl-oxobutyrate, and
Methyl 4-(3,4-dihydro-2,2-dimethyl-3-oxo-1,4[2H]-benzothiazin-6-yl-oxobutyrate.

EXAMPLE 51

4-(3,4-Dihydro-3-oxo-1,4[2H]-benzothiazin-7-yl)-3-methyl-4-oxobutyric acid 3,4-Dihydro-3-oxo-7-(1-oxopropyl)-1,4[2H]-benzothiazine (5.0 g) was added to a mixture of 2.25 ml of formalin solution and 2.72 g of dimethylamine hydrochloride in 7.5 ml of acetic anhydride and heated to 100° C. overnight. Acetone (20 ml) was added and the mixture heated at reflux for 15 minutes before the volitiles were removed at reduced pressure. The residue was taken up in 1N HCl and washed with ethyl acetate. The aqueous portion was chilled in ice and basified with 12.5N NaOH. The basic solution was extracted with ethyl acetate and dried over sodium sulfate. The solvent was removed and the residue taken up in acetone and 3 ml of methyl iodide added. The mixture was heated at reflux for three hours, then cooled, and the precipitate collected by filtration and washed with acetone to give 6.6 g of the quaternary ammonium salt of the mannich product.

The quaternary salt (6.6 g) was dissolved in 20% methanol/water and 3.8 g of potassium cyanide in 30 ml of water was added. The mixture was stirred at room temperature for 48 hours and the resultant precipitate collected by suction filtration to give 4-(3,4-dihydro-3-oxo-1,4[2H]-benzothiazin-7-yl)-3-methyl-4-oxobutyronitrile. The nitrile was heated to reflux in 200 ml of 6N HCl for 30 minutes, then cooled and diluted with an equal volume of ice water. The solid collected was used in Example 55.

EXAMPLE 52

Methyl 4-(3,4-dihydro-4-methyl-3-oxo-1,4[2H]-benzothiazin-7-yl)-3-methyl-4-oxobutyrate 4-(3,4-Dihydro-3-oxo-1,4[2H]-benzothiazin-7-yl)-3-methyl-4-oxobutyric acid (1.7 g) was dissolved in 50 ml of dimethylformamide and 0.23 g of 60% sodium hydride was added. After 30 minutes, 0.7 ml of methyl iodide was added and the mixture stirred at room temperature for three hours, then poured into 100 ml of ice water and extracted with ethyl acetate. The organic layer was washed with brine and dried over sodium sulfate and evaporated. The residue was chromatographed on a silica gel column eluted with 5% methanol in methylene chloride. The solvent was removed and the oil obtained was used in Example 56.

EXAMPLE 53

6-(3,4-Dihydro-3-oxo-1,4[2H]-benzothiazin-6-yl)-2,3,4,5-tetrahydropyridazin-3-one 4-(3,4-Dihydro-3-oxo-1,4[2H]-benzothiazin-6-yl)-4-oxobutyric acid (2.0 g) was suspended in 60 ml of ethanol and 1 ml of hydrazine added. The mixture was heated at reflux for three hours, then cooled slowly. Filtration gave 1.85 g of the title compound, mp 299°-302° C.

Theor. $C_{12}H_{11}N_3O_2S \cdot \frac{1}{2}H_2O$: C, 53.32; H, 4.48; N, 15.55. Found: C, 53.02; H, 4.26; N, 15.94.

The following compounds are prepared by the above procedure, using the appropriate starting materials:
4-(3,4-dihydro-2-methyl-3-oxo-1,4[2H]-benzothiazin-6-yl-oxobutyric acid, and
4-(3,4-dihydro-2,2-dimethyl-3-oxo-1,4[2H]-benzothiazin-6-yl-oxobutyric acid.

EXAMPLE 54

6-(3,4-Dihydro-4-methyl-3-oxo-1,4[2H]-benzothiazin-6-yl)-2,3,4,5-tetrahydropyridazin-3-one Methyl 4-(3,4-dihydro-4-methyl-3-oxo-1,4[2H]-benzothiazin-6-yl)-4-oxobutyrate (2.5 g) was heated at reflux in 70 ml of ethanol containing 1 ml of hydrazine for three hours. Filtration gave 1.5 g of the named compound, melting at 241°-242° C.

Theor. $C_{13}H_{13}N_3O_2S \cdot \frac{1}{4}H_2O$: C, 55.80; H, 4.88; N, 15.02. Found: C, 55.64; H, 4.87; N, 15.06.

The following compounds are prepared by the above procedure, using the appropriate starting materials:
4-(3,4-dihydro-2,4-dimethyl-3-oxo-1,4[2H]-benzothiazin-6-yl-oxobutyric acid, and
4-(3,4-dihydro-2,2,4-trimethyl-3-oxo-1,4[2H]-benzothiazin-6-yl-oxobutyric acid.

EXAMPLE 55

6-(3,4-Dihydro-3-oxo-1,4[2H]-benzothiazin-7-yl-2,3,4,5-tetrahydro-5-methylpyridazin-3-one 4-(3,4-Dihydro-3-oxo-1,4[2H]-benzothiazin-7-yl)-4-oxo-3-methylbutyric acid (1.2 g) was heated at reflux overnight in 50 ml of ethanol containing 0.2 ml of hydrazine. Filtration gave a white powder which was chromatographed on silica gel eluted with 5% methanol in methylene chloride, yielding 180 mg of the title compound melting >300° C.

Theor. $C_{13}H_{13}N_3O_2S \cdot \frac{1}{4}H_2O$: C, 55.80; H, 4.88; N, 15.02. Found: C, 56.13; H, 4.75; N, 15.00.

EXAMPLE 56

6-(3,4-Dihydro-4-methyl-3-oxo-1,4[2H]-benzothiazin-7-yl)-2,3,4,5-tetrahydro-5-methylpyridazin-3-one Methyl 4-(3,4-dihydro-4-methyl-3-oxo-1,4[2H]-benzothiazin-7-yl)-4-oxo-3-methylbutyrate (1.7 g) was heated at reflux overnight with 0.3 ml of hydrazine in 50 ml of ethanol. Filtration gave a white powder which was chromatographed on silica gel eluted with 5% methanol in methylene chloride, yielding 110 mg of the named compound, mp 193°-194.5° C.

Theor. $C_{14}H_{15}N_3O_2S$: C, 58.10; H, 5.24; N, 14.52. Found: C, 57.81; H, 5.42; N, 14.15.

EXAMPLE 57

3,4-Dihydro-3-oxo-6-oxopropyl-1,4[2H]benzothiazine

4-Amino-3-thiocyanatopropriophenone (prepared by the method of K. D. Luess and R. Pohloudek-Fabini in Arch. Pharm. 299(10), 878–884 (1966)) (35 g) was heated to reflux in 250 ml of water containing 90 g of sodium sulfide nonahydrate. The solution was cooled to room temperature and 60 ml of acetic acid was added. The precipitate that formed was collected and washed with water giving the mercapto compound.

4-Amino-3-mercaptopropiophenone was stirred in 200 ml of water containing 8.5 g of sodium hydroxide. The resultant mixture was filtered and 22 g of sodium chloroacetate added to the filtrate in 150 ml of water. After 30 minutes, 4 ml of acetic acid was added and the mixture heated to reflux. After 10 minutes, heat was removed and the mixture stirred at room temperature overnight. The yellow precipitate was collected by filtration and washed with water to give, after drying, 18.5 g of benzothiazine melting at 215°-220° C.

4-(3,4-Dihydro-3-oxo-1,4[2H]benzothiazin-7-yl)-4-oxobutyric acid was prepared by the same method as above. The starting material for this preparation was 4-aminophenyl-4-oxobutyric acid which is described by Thyes in *J. Med. Chem.* 26, 800 (1983). Thiocyanation was carried out by the method of K. D. Luess and R. Pohloudek-Fabini in *Arch. Pharm.* 299(10), 878–882 (1966).

EXAMPLE 58

Cardiotonic Activity

The cardiotonic activity of the compounds was determined in accordance with the method of Alousi, A. A., et al., *J. Cir. Res.* 45, 666 (1979). Basically, adult mongrel dogs were anesthetized with sodium pentobarbital and artificially respired. Arterial pressure was recorded via a femoral artery and the pressure pulse used to trigger a cardiotachometer for heart rate. Left ventricular pressure was measured with a Millar catheter and dP/dt was derived. Cardiac output was determined by measuring ascending aortic blood flow with an electromagnetic flow probe and myocardial contractile force was measured with a Walton Brodie strain gauge sutured to the right ventricle. Lead II EKG was also recorded. A standard does of dopamine was administered to assess myocardial responsiveness. Test compounds were administered by i.v. infusion or bolus administration and the effects on cardiovascular parameters were determined. Dose-related effects of the test compound on BP, HR, dP/dt max., C.F. and C.O. were compared to pretreatment control values and expressed as a percentage change. The results are shown in Table I.

EXAMPLE 59

Phosphodiesterase Inhibitory Activity

The phosphodiesterase inhibitory activity was determined in accordance with the method of Thompson, W. J. et al., in *Adv. Cycli. Nucleotide Res.*, Ed. Brooker, G. et al., Vol. 10, pp. 69–92 (1979). This assay measures the ability of compounds to inhibit cyclic nucleotide phosphodiesterase. This enzyme converts either cyclic AMP or cyclic GMP to the noncyclized AMP or GMP, respectively. Compounds were tested at various concentrations in the presence of cyclic AMP (0.10–1.0 μM containing 0.2 μCi $^3$H-cyclic AMP), enzyme, and 0.05M Tris-Cl buffer (pH 7.4, containing 5 mM MgCl$_2$). After a specified time, the reaction was stopped by heating to 100° C. for one minute. After cooling, 0.10 ml of a solution containing snake venom (1 mg/ml) was added and the reaction was allowed to proceed for 30 minutes. Termination of this reaction was accomplished by the addition of 1.0 ml of 33% Dowex slurry to separate the product from unconverted substrate. An aliquot was removed from the supernatant and quantitated by liquid scintillation spectrometry. The results are shown in Table I as the IC$_{50}$ which is the concentration (μM) of compound required to inhibit 50% of the cyclic nucleotide phosphodiesterase activity.

TABLE 1

| Compound (Example) | Dose (mpk)[a] | CF[b] | IC$_{50}$[c] |
|---|---|---|---|
| 8 | 1.87 | 98 | 9.5 |
| 9 | 1.87 | 62 | 100 |
| 10 | 1.87 | 18 | 50 |
| 11 | 1.87 | 41 | N.T.[d] |
| 12 | 1.87 | 92 | 50 |
| 13 | 1.87 | 71 | 100 |
| 14 | 1.87 | 30 | 80 |
| 15 | 1.87 | 125 | 8 |
| 16 | 1.87 | 173 | 30 |

TABLE 1-continued

| Compound (Example) | Dose (mpk)[a] | CF[b] | IC$_{50}$[c] |
|---|---|---|---|
| 17 | 1.87 | 62 | 4 |
| 18 | 0.47 | 50 | 8 |
| 19 | 0.47 | 98 | 40 |
| 20 | 1.87 | 71 | 630 |
| 21 | 0.47 | 74 | 18 |
| 22 | 0.47 | 136 | 2 |
| 23 | 0.47 | 134 | 8 |
| 24 | 0.47 | 54 | 14 |
| 25 | 0.47 | 31 | 13 |
| 26 | 0.47 | 156 | 5 |
| 27 | 0.47 | 117 | 6 |
| 28 | 0.47 | 46 | 15 |
| 29 | 0.47 | 12 | 56 |
| 30 | 0.47 | 124 | 20 |
| 31 | 0.47 | 33 | 38 |
| 33 | 0.47 | 8 | 30 |
| 36 | 0.47 | 40 | 24 |
| 37 | 0.47 | 4 | 8 |
| 38 | 0.47 | 24 | 31 |
| 39 | 0.47 | 18 | 28 |
| 40 | 0.47 | 22 | 26 |
| 41 | 0.47 | 60 | 7 |
| 42 | 0.47 | 15 | 100 |
| 43 | 0.47 | 104 | 35 |
| 46 | 0.075 | 130 | 0.3 |
| 47 | 0.075 | 109 | 0.3 |
| 53 | 0.075 | 21 | 25 |
| 54 | 0.075 | 11 | 22 |
| 55 | 0.035 | 160 | <0.1 |
| 56 | 0.027 | 32 | <0.1 |

[a]I.V. dose used for cardiotonic activity assay.
[b]Percent increase in cardiac force.
[c]Micromolar concentration for 50% inhibition of cyclic nucleotide activity.
[d]Not tested.

What is claimed is:

1. A compound of the formula

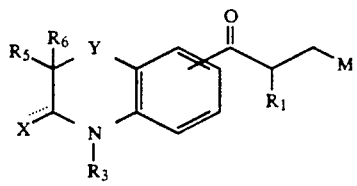

where
R$_1$, R$_3$, R$_5$ and R$_6$ are independently H, C$_{1-6}$ straight- or branched-chain alkyl or C$_{3-6}$ cycloalkyl;
Y is S or O;
X is H$_2$ or O; and M is —CN or mono- or di-C$_{1-6}$ alkyl amino; and the quaternary ammonium salts thereof provided that when M is mono- or di-C$_{1-6}$ alkyl amino the substituent is attached to the benzoxazine moiety at the 7-position.

2. A compound of the formula

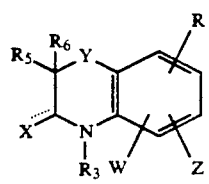

where
X is H$_2$ or O;
Y is O or S;

$R_3$ is H, $C_{1-6}$ straight- or branched-chain alkyl or $C_{3-6}$ cycloalkyl, and when X is $H_2$, $R_3$ is also $C_{2-6}$ acyl, arylacyl or $C_{1-6}$ alkylsulfonyl;

$R_5$ and $R_6$ are independently H, $C_{1-6}$ straight- or branched-chain alkyl or $C_{3-6}$ cycloalkyl;

R, W and Z are independently H, $C_{1-6}$ straight- or branched-chain alkyl, $C_{2-6}$ acyl or —C(O)CHR$_4$CH$_2$C(O)OR$_7$ provided that one of R, W and Z is —C(O)CHR$_4$CH$_2$C(O)OR$_7$;

$R_4$ is H, $C_{1-6}$ straight-branched-chain alkyl or $C_{3-6}$ cycloalkyl; and $R_7$ is H or $C_{1-6}$ straight- or branched-chain alkyl;

provided that when one of R, W and Z is —C(O)CHR$_4$CH$_2$C(O)OR$_7$ then the other cannot be —C(O)CH$_4$CH$_2$C(O)OR$_7$ and R, W or Z is not —C(O)CHR$_4$CH$_2$C(O)OR$_7$ in the 6 position.

3. A compound of the formula

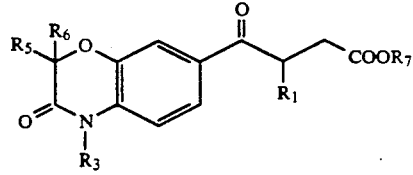

where
$R_1$, $R_3$, $R_5$ and $R_6$ are independently H, $C_{1-6}$ straight- or branched-chained alkyl or $C_{3-6}$ cycloalkyl; and
$R_7$ is H or $C_{1-6}$ straight- or branched-chain alkyl.

4. The compound of claim 3 which is 4-oxo-4-(3,4-dihydro-3-oxo-1,4(2H)-benzoxazin-7-yl)-3-methyl-butyric acid.

5. The compound of claim 3 which is methyl 4-oxo-4-(3,4-dihydro-4-methyl-3-oxo-1,4(2H)-benzoxazin-7-yl)-3-methylbutyrate.

6. The compound of claim 1 which is 4-oxo-4-(3,4-dihydro-3-oxo-1,4(2H)-benzoxazin-7-yl)-3-methyl-butyronitrile.

7. The compound of claim 1 which is [3-oxo-3-(3,4-dihydro-4-methyl-3-oxo-1,4(2H)-benzoxazin-7-yl)-2-methylpropyl]trimethylammonium iodide.

8. The compound of claim 1 which is [3-oxo-3-(3,4-dihydro-4-methyl-3-oxo-1,4(2H)-benzoxazin-7-yl)-2-methylpropyl]dimethylamine.

* * * * *